United States Patent [19]

Aotani et al.

[11] Patent Number: 4,559,303
[45] Date of Patent: Dec. 17, 1985

[54] CARRIER COMPOSED OF PARTICULATE POLYMER

[75] Inventors: Seiji Aotani, Yokohama; Hisanori Kanayama, Machida, both of Japan

[73] Assignee: Japan Synthetic Rubber Co., Ltd., Tokyo, Japan

[21] Appl. No.: 496,502

[22] Filed: May 20, 1983

[30] Foreign Application Priority Data

May 28, 1982 [JP] Japan .................. 57-89707

[51] Int. Cl.$^4$ .................... C12N 11/08; G01N 33/54; A61K 31/78
[52] U.S. Cl. ........................ 435/180; 435/7; 435/174; 436/531; 436/534; 436/823; 424/81
[58] Field of Search ............. 435/7, 174, 180; 436/531, 534, 823; 424/81

[56] References Cited

U.S. PATENT DOCUMENTS

| | | | |
|---|---|---|---|
| 3,794,563 | 2/1974 | Barker et al. | 436/531 |
| 3,932,321 | 1/1976 | Maki et al. | 260/17.4 R |
| 4,138,383 | 2/1979 | Rembaum et al. | 436/531 |
| 4,352,884 | 10/1982 | Nakashima et al. | 435/180 |
| 4,418,152 | 11/1983 | Hosaka et al. | 436/531 |
| 4,446,275 | 5/1984 | Filka et al. | 435/179 |

*Primary Examiner*—Christine M. Nucker
*Attorney, Agent, or Firm*—Oblon, Fisher, Spivak, McClelland & Maier

[57] ABSTRACT

A carrier composed of particulate polymer of at least one monomer represented by the general formula:

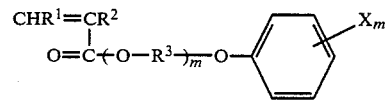

wherein $R^1$ and $R^2$, which may be the same or different, are hydrogen atoms or alkyl groups having 1 to 4 carbon atoms; $R^3$ is a straight-chain or branched alkylene group having 2 or 3 carbon atoms, which group may be substituted by a hydroxyl group; X's, which may be the same or different, are halogen atoms; m is zero or an integer of 1 to 10; and n is an integer of 1 to 5, or a particulate polymer of said monomer and at least one other copolymerizable monomer. Said carrier is suitable for supporting a biological substance such as an immunoreactive substance, an enzyme, a cell, a cell-discriminating substance, and the like, particularly an immunoreactive substance.

11 Claims, No Drawings

CARRIER COMPOSED OF PARTICULATE POLYMER

This invention realtes to a carrier suitable for supporting a biological substance such as an immunoreactive substance, an enzyme, a cell, a cell-discriminating substance and the like, particularly an immunoreactive substance.

It has become an important clinical examination means to detect an immunoreactive substance such as an antigen or antibody by immunological reaction with a corresponding immunoreactive substance, such as antibody or antigen, supported on a particulate carrier. There is also often used a particulate carrier having supported thereon a substance capable of selectively combining with specific cells, i.e., a cell-discriminating substance in discriminating or separating said cells. Further, it is a conventional technique to conduct enzyme reaction on a particulate carrier having supported thereon an enzyme or to cultivate cells on the surface of a particulate carrier having supported thereon the said cells as a cell-culturing bed. As the particulate carriers used for such purposes, there have heretofore been used erythrocytes of a human being, a sheep, a domestic fowl, an alligator or the like and fine particles of a polymer such as a polystyrene, a styrene-(meth)acrylic acid copolymer. For example, a carrier having supproted thereon an immunoreactive substance is used as a reagent, and an immunological reaction is effected by using a dispersion of this reagent in a liquid medium (hereinafter referred to as the sensitizing latex), and the change of states of the sensitizing latex, i.e., the aggregation state, the sedimentation state, the dispersion state or the like of the sensitizing latex is observed, whereby the presence of the corresponding immunoreactive substance can be determined.

When a test liquid has added thereto a labeled substance to be detected as in enzyme immunoassay, radio immunoassay and the like, the amount of the substance to be detected which has reacted with the particles can be determined by separating the particles. Further, when an antigenic group or an antibody group is present in cells, only the said cells can selectively be collected by use of a carrier having supported thereon an antibody or antigen corresponding to said antigenic group or antibody group, respectively.

In these methods, what is required for the particulate carrier having supported thereon a biological substance or the like is that the carrier is stable without causing non-specific reaction, non-specific aggregation and the like; that the carrier can easily be separated from a liquid medium; and that when the carrier is reacted in the form of a sensitizing latex with a substance to be detected, the change in stage of the sensitizing latex due to said reaction can simply be detected.

Sensitizing latexes in which a carrier consisting of erythrocyte is used have heretofore been used as those in simple detecting methods such as slide method, microtiter method and the like because the change in state of the sensitizing latex can be observed in a relatively short time by reacting the sensitizing latex with a substance to be detected. However, since erythrocytes are used therein, the qualities of the sensitizing latexes are greatly different, the non-specific aggregation tends to take place, and the storage thereof is difficult. For such reasons, it has been desired that said carrier be replaced by a stable carrier. Therefore, fine particles of a polymer such as polystyrene are used as a carrier to be substituted for the carrier consisting of erythrocyte, and are allowed to have supported thereon a bilogical substance such as an immunoreactive substance or the like by physically adsorbing it thereon or chemically combining it therewith, because they are excellent in stability and have no variation in quality.

However, carriers consisting of a polymer such as polystyrene are disadvantageous in that when they are used in the form of a sensitizing latex and a substance to be detected is detected by observing the aggregation state or sedimentation state of the sensitizing latex, a period of time as long as from ten and several hours to several tens of hours is required.

The object of this invention is to provide a carrier suitable for supporting a biological substance or the like thereon, which carrier consists essentially of specific particulate polymer and which enabled easy observation of the change in the state of a sensitizing latex caused by reaction thereof with a substance to be detected, as in the case of a sensitizing latex in which a carrier consisting of erythrocyte is used and which is stable and has no variation in quality, like carriers comprising a polymer such as polystyrene or the like.

According to this invention, there is provided a carrier consisting essentially of a particulate polymer obtained by polymerizing a monomer represented by the general formula:

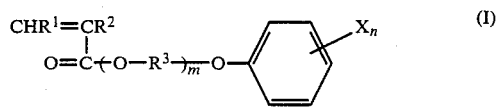

wherein $R^1$ and $R^2$, which may be the same or different, are hydrogen atoms or alkyl groups having 1 to 4 carbon atoms; $R^3$ is a straight-chain or branched alkylene group having 2 or 3 carbon atoms, which group may be substituted by a hydroxyl group; X's are the same or different halogen atoms; m is zero or an integer of 1 to 10; and n is an integer of 1 to 5, or by polymerizing said monomer and at least one other copolymerizable monomer.

Each of $R^1$ and $R^2$ in the monomer of the general formula (I) used in this invention is preferably a hydrogen atom or a methyl group; $R^3$ is preferably an ethylene group or a propylene group; X is preferably a chlorine atom or a bromine atom; m is preferably 0 or 1; and n is preferably 3 to 5. Concrete examples of the monomer represented by the general formula (I) include monofluorophenyl (meth)acrylate, monochlorophenyl (meth)acrylate, trichlorophenyl (meth)acrylate, pentachlorophenyl (meth)acrylate, monobromophenyl (meth)acrylate, tribromophenyl (meth)acrylate, pentabromophenyl (meth)acrylate, monoiodophenyl (meth)acrylate, 2-(tribromophenoxy)ethyl (meth)acrylate, 2-(tribromophenoxyethoxy)ethyl (meth)acrylate, 2-(pentachlorophenoxy)propyl (meth)acrylate, 1-(tribromophenoxy)-2-hydroxypropyl (meth)acrylate, and the like.

By polymerizing these monomers with other copolymerizable monomers, the characteristics of a carrier such as water-attracting ability, water-repellency, functionality, degree of charge, and the like of the surface of polymer particles obtained can be varied and the specific gravity of the resulting polymer particles can be controlled.

As the aforesaid other copolymerizable monomer, there may be exemplified, for example, aromatic alkenyl compounds, α,β-unsaturated carboxylic acids or their esters or amides, α,β-unsaturated nitrile compounds, halogenated vinyl compounds, conjugated diene compounds and lower fatty acid vinyl ester compounds, such as styrene, chlorostyrene, α-methylstyrene, divinylbenzene, sodium styrenesulfonate, (meth)acrylic acid, methyl (meth)acrylate, ethyl (meth)acrylate, 2-hydroxyethyl (meth)acrylate, glycidyl (meth)acrylate, ethylene glycol di-(meth)acrylate, allyl (meth)acrylate, (meth)acrylonitrile, (meth)acrolein, (meth)acrylamide, N-methylol (meth)acrylamide, methylene bis(meth)acrylamide, butadiene, isoprene, vinyl acetate, vinylpyridine, N-vinylpyrrolidone, vinyl chloride, vinylidene chloride, vinyl bromide, and the like.

As the method for obtaining the polymer of this invention, there may be used, for example, a radical polymerization method, concretely, an emulsion polymerization method, an emulsion polymerization method using no emulsifier (soap-free polymerization method), a suspension polymerization method, a solution polymerization method, a solution-precipitation polymerization method, a seed polymerization method, or the like, though the soap-free polymerization method, the solution-precipitation polymerization method or a seed polymerization method is advantageous, because a polymer can be formed in the form of fine particles, and hence, the removal of impurities is easy.

In the case of the soap-free polymerization method, there can be obtained, for example, polymer particles having the same spherical shape having a controlled particle diameter in a range of 0.05 to 2 μm and a narrow diameter distribution by varying the method of adding the monomer, the kind and amount of the monomer, the amount of a polymerization initiator, and the like. In the case of the soap-free polymerization method, there may be used, as a medium, water or a mixed solution of water and a water-soluble organic solvent such as methanol, ethanol, acetone, tetrahydrofuran or the like, and the employment thereof is effective, for example, for controlling the particle diameter and the polymerization rate.

In the case of the solution-precipitation polymerization method, polymer particles having a diameter ranging from 0.1 to 10 μm can be obtained by varying the kind and amount of a solvent. In this case, a solvent in which the starting monomer can be dissolved but the resulting polymer is cannot be dissolved is selected from, for example, lower alcohols, ethers, ketones, esters, hydrocarbons and halogenated hydrocarbons, such as methanol, ethanol, isopropanol, anisole, dibutyl ether, acetone, methyl ethyl ketone, methyl isobutyl ketone, acetophenone, methyl acetate, ethyl acetate, n-butyl acetate, ethyl propionate, n-hexane, cyclohexane, benzene, dichloroethane, chloroform, chlorobenzene, and the like. However, the solubility of the monomer is not critical, and it is sufficient that the monomer can be dissolved in the solvent upon heating. Moreover, an ionic monomer such as sodium styrenesulfonate or the like is sometimes polymerized without dissolving it in a solvent. In this polymerization method, when a polyfunctional monomer having a plurality of vinyl groups is copolymerized with the above-mentioned monomer, the diameter of the resulting polymer particles can easily by increased.

According to a seed polymerization method, such as a method for polymerizing a monomer in the presence of fine particles such as polymer particles or the like by a soap-free polymerization method, a method for suspension-polymerizing a monomer adsorbed on and/or permeated into fine particles in a liquid medium such as water, the particle diameter of polymer particles can be further increased and the particle diameter distribution can be narrowed.

The aforesaid soap-free polymerization method is particularly preferred as the polymerization method, and is advantageous in that the resulting polymer particles have a narrow diameter distribution and the same shape.

When a monomer represented by the general formula (I) is polymerized with an other copolymerizable monomer, it is preferable that the monomer represented by the general formula (I) be polymerized in an amount of 10 mole % or more, in particular, 15 to 60 mole %. When the polymerization proportion of the monomer represented by the general formula (I) is low, the resulting polymer particles has a lowered supporting ability as a carrier and cannot have a markedly increased specific gravity as a carrier. For using the resulting polymer as the carrier of this invention, its particle diameter is preferabvle 0.1 to 10 μm, particularly preferably 0.3 to 1 μm, and its specific gravity is preferably 1.2 to 2 g/cm$^3$, particularly preferably 1.3 to 1.8 g/cm$^3$. When the particle diameter or specific gravity of the carrier is too small or too large, it becomes difficult to observe the change in state of a sensitizing latex caused by reaction of the carrier with a substance to be detected, when the carrier is used in the form of the sensitizing latex.

The method of supporting a biological substance, for example, an immunoreactive substance, on the carrier of this invention is not critical, and an example is a method comprising contacting the carrier with the immunoreactive substance in a liquid medium, separating and recovering the carrier, and if necessary, washing it with a detergent. In this case, the liquid medium may vary depending upon the kind of the immunoreactive substance though there may preferable be used, for example, a phosphate-buffer saline solution, a glycine buffer saline solution, and a medium consisting of a mixture of them with a nonionic surfactant, serum albumin or the like. Furthermore, as the detergent, there may be usually used a liquid medium for use in supporting the immunoreactive substance on the carrier though it is not critical.

The carrier of this invention, when used in the form of a sensitizing latex, can make it easy to observe the change in state of a sensitizing latex caused by reaction of the carrier with a substance to be detected, and has an excellent stability and no variation in quality, and the surface characteristics of the carrier can easily be varied by properly selecting the kinds of monomers to be polymerized.

Particularly, the carrier of this invention is excellent in the amount, per unit area, of a biological substance or the like to be supported thereon, and moreover, it hardly undergo non-specific aggregation and is excellent in dispersion-stability even when it has supported thereon a biological substance or the like.

Since the carrier of this invention has a large specific gravity, it is very easy to separate the carrier from a liquid medium such as water or the like, and when used in the form of a sensitizing latex or the like, it is very advantageous in the case where sedimentation accompanies the detection of a substance to be detected. For example, when a reagent prepared by supporting an immunoreactive substance on the carrier of this invention is used as the sensitizing latex in a microtiter method, the measurement, for which it has conventionally taken ten and several hours to several tens of hours, can be finished in about 30 minutes to several hours, and the separation of the particles by centrifugation or the like also can be finished in a very short time.

Examples of the biological substance to be supported on the carrier of this invention include immunoreactive substances such as surface antigen of B type hepatitis (HBs antigen), anti-HBs antibody, human chorionic gonadotropin (HCG antigen), anti-HCG antibody, immunoglobulin G, mycoplasma antigen, nucleic acid, nuclear protein, estrogen, anti-estrogen antibody and the like; enzymes such as glucose isomerase, glucose oxidase, α-amylase, papain, aminoacylase and the like; and cells requiring a solid surface for their growth, such as fetal pneumonocyte, renal cell, fibroblast and the like. These substances may properly be selected depending on purposes.

This invention is explained below referring to Examples. However, this invention is not limited to the Examples.

EXAMPLE 1 [PRODUCTION OF PARTICLES FOR CARRIER]

(1) A mixed solution of 64 g of pentachlorophenyl acrylate, 32 g of styrene, 3 g of methacrylic acid and 1 g of t-dodecylmercaptan was continuously dropped with stirring into 600 ml of water at 80° C. containing 1 g of potassium persulfate over a period of 4 hours.

After completion of the dropping, the stirring was continued to conduct further polymerization (soap-free polymerization) for an additional 2 hours, whereby polymer particles having an average diameter of 0.4 μm were obtained in the form of a latex at a polymerization conversion of 98%. The polymer particles obtained were purified by washing, sufficiently dispersed by supersonic treatment, and passed through pores having a diameter of 7 μm, thereby removing aggregates of particles and particles having a large diameter. Subsequently, the concentration of the residue was adjusted, and the thus treated polymer particles were used as a carrier in the form of an aqueous dispersion. The polymerization ratio between the above-mentioned monomers for this carrier was as follows: pentachlorophenyl acrylate/styrene/methacrylic acid=0.37/0.55/0.8 (molar ratio). (2) In 2 liters of ethanol were dissolved 72 g of tribromophenyl acrylate, 26 g of styrene and 2 g of divinylbenzene, and 2 g of azobisisobutyronitrile was added, after which the resulting mixture was subjected to polymerization (precipitation polymerization) at 75° C. with stirring to deposit a polymer in the form of fine particles. The stirring was continued for 4 hours to obtain polymer particles having an average diameter of 1.0 μm in the form of a dispersion at a polymerization conversion of 93%. Since the polymer particles settled immediately, they were separated from the ethanol by a decantation method, purified, and then treated in the same manner as in above (1), after which the polymer particles were used as a carrier in the form of an aqueous dispersion. The polymerization ratio between the above-mentioned monomers for this carrier was as follows: tribromophenyl acrylate/ styrene/divinylbenzene=0.41/0.55/0.03 molar ratio). (3) To 300 g of a 10% by weight aqueous dispersion of the polymer particles obtained in above (1) were added 30 g of monomers of the same composition as in above (1) and 0.6 g of benzoyl peroxide, and the resulting mixture was stirred at room temperature for 2 hours and then at 70° C. for 5 hours to conduct polymerization. After completion of the polymerization (seed polymerization), the resulting polymer particles were purified, after which they were treated in the same manner as in above (1), and then used as a carrier in the form of an aqueous dispersion. The average particle diameter of this carrier was 0.55 μm, and its particle diameter distribution was narrower than that of the carrier in above (1). (4) A mixed solution of 30 g of 2-tribromophenoxyethyl acrylate, 21 g of styrene and 2 g of methacrylic acid and a mixed solution of 0.3 g of ammonium persulfate and 40 ml of water were continuously dropped from the respective vessels with stirring over a period of 3 hours into a mixed medium consisting of 160 ml of water and 50 ml of acetone which was maintained at 60° C.

After completion of the dropping, the stirring was further continued to conduct further polymerization (soap-free polymerization) for an additional two hours to obtain polymer particles having an average diameter of 1.10 μm in the form of a latex. The polymer particles obtained were purified, and then treated in the same manner as in above (1), after which they were used as a carrier in the form of an aqueous dispersion. The polymerization ratio between the above-mentioned monomers for this carrier was as follows: 2-tribromophenoxyethyl acrylate/styrene/methacrylic acid=0.29/0.1/0.03 (molar ratio).

EXAMPLE 2 [CHARACTERISTICS OF CARRIER]

The characteristics of the carriers obtained in Example 1 were examined in the following manner, and at the same time, the caracteristics of carboxy-modified polystyrene particles having an average diameter of 0.5 μm were examined for comparison:

(1) Sedimentation time

An aqueous dispersion having a carrier concentration of 0.1% by weight was placed in a V-type well for a microtiter, and the time required until a round spot could be clearly observed was measured.

(2) Amount of protein adsorbed

To 2 ml of an aqueous dispersion having a carrier concentration of 0.5% by weight was added 2 ml of a solution of bovine serum γ-globulin in a phosphate buffer which had a concentration of 500 μg/ml, and they were mixed for 1 hour. Subsequently, the γ-globulin concentration in the supernatant was measured at a wavelength of 280 nm by means of a spectrophotometer, and the amount of γ-globulin adsorbed per unit area of the carrier was calculated from the difference in absorbance between the sample and a blank.

(3) Average particle diameter

Measured by observation under an electron microscope.

(4) Specific gravity

Measured by a density-gradient tube method. The results obtained are shown in Table 1.

TABLE 1

| Carrier | Average particle diameter (μm) | Specific gravity (g/cm³) | Sedimentation time | Amount of protein adsorbed (μg/cm³) |
| --- | --- | --- | --- | --- |
| Carrier obtained in Example 1-(1) | 0.40 | 1.56 | 360 min | 0.80 |
| Carrier obtained in Example 1-(2) | 1.00 | 1.69 | 110 min | 1.35 |
| Carrier obtained in Example 1-(3) | 0.55 | 1.56 | 240 min | 0.95 |
| Carrier obtained in Example 1-(4) | 1.10 | 1.45 | 160 min | 0.85 |
| Carboxy-modified polystyrene particles | 0.5 | 1.05 | >48 hrs | 0.25 |

EXAMPLE 3 [MEASUREMENT OF IMMUNOREACTIVE SUBSTANCE]

Each of the carriers obtained in Example 1-(1) and (2) was dispersed in a 1/60 M phosphate buffer saline solution containing 0.15 mole of sodium chloride and having a pH of 7.2 (hereinafter referred to as "PBS") in such a proportion that the solids concentration was 0.25% by weight. Thereto was added the same volume of a PBS solution of an antigen, thermally aggregated human IgG (hereinafter referred to as "agr-IgG") which had a concentration of 50 μg/ml. Each of the thus obtained mixtures was gently stirred for 2 hours to carry out a treatment for supporting the antigen on each of the carriers, washed with PBS to remove the unadsorbed antigen, and then diluted with a diluent prepared by adding rabbit serum to PBS so that the concentration became 1% by weight (hereinafter referred to simply as "the diluent"), whereby a sensitizing latex having a solids concentration of 0.25% by weight was prepared. The agr-IgG used here was an antigen obtained by dissolving human IgG in PBS so that the concentration became 10 mg/ml, and heating the resulting solution at a temperature of 63° C. for 15 minutes.

For comparison, a comparative sensitizing latex was prepared in the same manner as described above, except that commercially available carboxy-modified polystyrene particles having an average diameter of 0.5 μm were substituted for the carriers obtained in above Example 1.

According to a microtiter method, serum of a rheumatic factor-positive patient was subjected to serial two-fold dilution with 0.025 ml of the diluent each time on a V-type well for a microtiter, and 0.025 ml of the sensitizing latex described above was added dropwise to each dilution after which they were sufficiently mixed. The mixtures thus obtained were then allowed to stand at room temperature, and the aggregation image at each well bottom was judged with the naked eye at the time when the judgment became possible.

As shown in Table 2, it can be seen that when the carrier of this invention was used, the time required for the measurement was greatly reduced and the sensitivity was good.

TABLE 2

| Carrier | Dilution ratio | | | | | Judgment time |
| --- | --- | --- | --- | --- | --- | --- |
| | 800 | 1600 | 3200 | 6400 | 12800 | |
| Carrier obtained in Example 1-(1) | +++ | +++ | ++ | ± | − | 240 min |

TABLE 2-continued

| Carrier | Dilution ratio | | | | | Judgment time |
| --- | --- | --- | --- | --- | --- | --- |
| | 800 | 1600 | 3200 | 6400 | 12800 | |
| Carrier obtained in Example 1-(2) | +++ | +++ | +++ | ++ | − | 60 min |
| Carboxy-modified polystyrene particles | +++ | +++ | + | − | − | 24 hrs |

Note:
The symbols + + +, + +, +, ± and − show the sedimentation states of particles: + + + shows the largest area and − shows the smallest spot, between which + +, + and ± exist in this order.

EXAMPLE 4 [MEASUREMENT OF IMMUNOREACTIVE SUBSTANCE]

With 1 ml of a PBS dispersion having a carrier concentration of 0.25% by weight prepared by use of the carrier obtained in Example 1-(3) was mixed 1 ml of a solution prepared by diluting human glomerulus basement membrane antigen with PBS to 80 volumes (hereinafter referred to as "the diluted antigen"), and 1 ml of a 0.125% by weight aqueous chromium chloride solution was added, after which the resulting mixture was gently stirred at 20° C. for 2 hours to support the antigen on the carrier. Subsequently, the mixture was washed with PBS and the diluent, and then diluted with 1 ml of the diluent to prepare a sensitizing latex. The antigen used here was a supernatant obtained by separating glomerulus basement membrane from the kidney of a person died of illness, treating it overnight with collagenase at 37° C., and then centrifuging it at 30,000 r.p.m. for 60 minutes.

Separatley, 1 ml of a PBS dispersion of formalin-anchored sheep erythrocyte having a concentration of 0.5% by weight was mixed with 1 ml of a PBS solution of tannic acid having a concentration of 0.01 mg/ml, and the resulting mixture was allowed to stand at 37° C. for 20 minutes and washed with PBS, after which a PBS dispersion of the tannic acid-treated erythrocyte having a concentration of 0.5% by weight was obtained. With 1 ml of the dispersion of the tannic acid-treated erythrocyte was mixed 1 ml of the aforesaid diluted antigen, and the mixture thus obtained was allowed to stand at 37° C. for 40 minutes to support the antigen on the erythrocyte. Subsequently, the mixture was washed with PBS and the diluent, after which a comparative sensitizing latex having a concentration of 0.5% by weight was prepared.

According to a mirotiter method, an antibody prepared by immunizing a rabit with human glomerulus basement membrane was subjected to serial two-fold dilution with 0.025 ml of the diluent each time on a V-type well for a microtiter, and 0.025 ml of the aforesaid sensitizing latex was added dropwise to each dilution, after which they were sufficiently mixed. The mixture thus obtained were then allowed to stand at room temperature, and the aggregation image at each well bottom was judged with the naked eye at the time when the judgment became possible. The results obtained are shown in Table 3. When the comparative sensitizing latex was used, there was required, for preventing non-specific reactions from occuring, a procedure comprising adding the same amount of the washed anchored sheep erythrocyte sediment to each of the solutions prepared by diluting the antibody, treating each of the mixture thus obtained at room temperature for 60 minutes, centrifuging it, and adding the sensitizing latex dropwise to the resulting supernatant.

TABLE 3

| Carrier | Dilution ratio | | | Judgment time |
|---|---|---|---|---|
| | 16000 | 32000 | 64000 | |
| Carrier obtained in Example 1-(3) | + | ± | − | 3 hrs |
| Sheep erythrocyte | + | ± | − | 5 hrs |

Note:
+, ± and − have the same meanings as defined in Table 2.

It can be seen from Table 3 that the carrier of this invention can be used, like sheep erythrocyte, as a carrier, requires a shorter judgment time than the sheep erythrocyte, and requires no pretreatment for preventing non-specific reactions from occuring.

EXAMPLE 5 [MEASUREMENT OF IMMUNOREACTIVE SUBSTANCE]

The carrier obtained in Example 1-(4) was dispersed in PBS so that the solids concentration became 0.5% by weight, and methylate bovine serum albumin was mixed therewith so that the concentration became 10 μg/ml, after which the resulting mixture was allowed to stand for 2 hours, and then washed with PBS. Thereto was added the same amount of a PBS solution of polyinosinicpolycytidylic acid [double-stranded RNA (ds-RNA)](hereinafter referred to as "PIPC") having a concentration of 100 μg/ml, and the mixture thus obtained was gently stirred for 2 hours to support the antigen on the carrier. Subsequently, the mixture was washed with PBS to remove the unadsorbed antigen, and then diluted with the diluent to prepare a sensitizing latex having a solids concentration of 0.1% by weight.

Subsequently, according to a microtiter method, serum of a systemic erythematodes-positive patient was subjected to serial two-fold dilution with 0.025 ml of the diluent each time on a V-type well for a microtiter, and 0.025 ml of the sensitizing latex described above was added dropwise to each dilution, after which they were sufficiently mixed. The thus obtained mixtures were then allowed to stand at room temperature, and the aggregation image at each well bottom was judged with the naked eye at the time when the judgment became possible. The results obtained are shown in Table 4.

TABLE 4

| Carrier | Dilution ratio | | | Judgment time |
|---|---|---|---|---|
| | 160 | 320 | 640 | |
| Carrier obtained in Example 1-(4) | ++ | ± | − | 1 hr |

Note:
++, ± and − have the same meanings as in Table 2.

What is claimed is:

1. A carrier having a biological substance supported thereon, wherein said carrier consists essentially of polymer particles produced by Polymerizing a monomer having the formula:

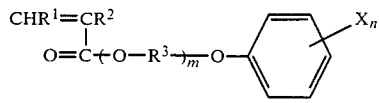

wherein $R^1$ and $R^2$, which are the same or different, are hydrogen atoms or alkyl groups having 1 to 4 carbon atoms; $R^3$ is a straight-chain or branched alkylene group having 2 or 3 carbon atoms, which is unsubstituted or substituted by a hydroxyl group; X is one or more of the same or different halogen atoms; m is zero or an integer of 1 to 10; and n is an integer of 1 to 5, or by polymerizing said monomer with at least one other vinyl monomer copolymerizable therewith; and wherein said biological substance is selected from the group of immunoreactive substances, enzymes, cells or cell-discriminating substances.

2. The carrier according to claim 1, which has a particle diameter of 0.1–10 μm.

3. The carrier according to claim 1, which has a particle diameter of 0.3 to 1 μm.

4. The carrier according to claim 2, which has a specific gravity of 1.2 to 2 g/cm³.

5. The carrier according to claim 3, which has a specific gravity of 1.3 to 1.8 g/cm³.

6. A carrier according to claim 1, wherein the said other vinyl monomer is selected from the group consisting of aromatic alkenyl compounds, α,β-unsaturated carboxylic acid, esters of α,β-unsaturated carboxylic acid, α,β-unsaturated carboxylic amides, α,β-unsaturated nitrile compounds, vinyl halides, conjugated diene compounds, and vinyl esters of fatty acids.

7. The carrier according to claim 1, wherein the amount of the monomer represented by the formula (I) is at least 10 mole % of the total amount of, the monomers.

8. The carrier according to claim 1, wherein the amount of the monomer represented by the formula (I) is 15 to 60 mole % of the total amount of the monomers.

9. The carrier according to claim 1, wherein the monomer represented by the formula (I) is monofluorophenyl (meth)acrylate, trichlorophenyl (meth)acrylate, pentachlorophenyl (meth)acrylate, monobromophenyl (meth)acrylate, tribromophenyl meth)acrylate, pentabromophenyl (meth)acrylate, monoiodophenyl (meth)acrylate, 2-(tri-bromophenoxy)ethyl (meth)acrylate, 2-(tribromophenoxyethoxy)ethyl (meth)acrylate, 2-(pentachlorophenoxy)propyl (meth)acrylate or 1-(tribromophenoxy)2-hydroxypropyl (meth)acrylate.

10. The carrier according to claim 1, wherein the polymer particles are those obtained by a soap-free polymerization method, a solution-precipitation polymerization method or a seed polymerization method.

11. A reagent for detecting an antigen or antibody consisting of a carrier consisting essentially of polymer particles obtained by polymerizing a monomer having by the formula:

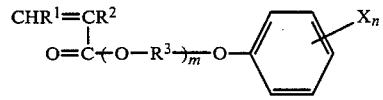

wherein $R^1$ and $R^2$, which are the same or different, are hydrogen atoms or alkyl groups having 1 to 4 carbon atoms; $R^3$ is a straight-chain or branched alkylene group having 2 or 3 carbon atoms, which is unsubstituted or substituted by a hydroxyl group; X is one or more of the same or different halogen atoms; m is zero or an integer of 1 to 10; and n is an integer of 1 to 5; or by polymerizing said monomer with at least one other vinyl monomer copolymerizable therewith; and wherein said biological substance is an immunoreactive substance.

* * * * *